July 14, 1959 J. L. SCHWOERER Plant Pat. 1,852
CAMELLIA PLANT
Filed May 19, 1958
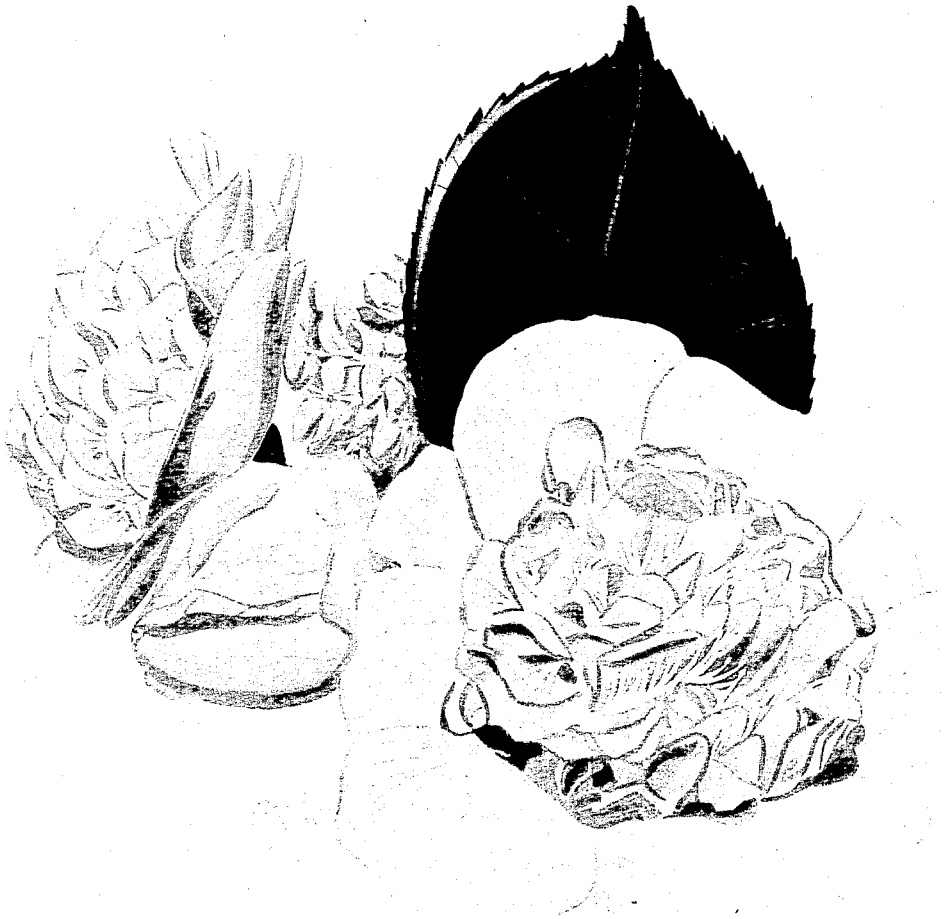
INVENTOR
John Lester Schwoerer
BY J. Nadams
Attorney United States Patent Office Plant Pat. 1,852
Patented July 14, 1959

1,852

CAMELLIA PLANT

John Lester Schwoerer, Oakland, Calif.

Application May 19, 1958, Serial No. 736,419
1 Claim. (Cl. 47—60)

This invention and discovery relates to a new and distinct variety of Camellia plant belonging to that division of the Camellia species known as the *japonica*.

It was discovered as a seedling resulting from a chance pollinated cross made in the garden of my home in Oakland, California. There is strong reason to believe that the pollen parent was the *Camellia japonica*, variety Kumasaka. The seed was picked by me from *Camellia japonica*, variety Princess Bachiocchi. The varieties "Kumasaka" and "Princess Bachiocchi" are not patented.

Broadly, this new variety of Camellia plant is distinguishable from the parent plants as well as from other known varieties mainly by its large, semi-double to anemone-peony form of bloom; center petals heavily convoluted with stamens and numerous petaloids intermixed; outer guard petals flat, in a single row; its peony-like center of unusual depth; and by the setting of many flower buds, which are of unusually large size. Its color is rose, with petals veined in slightly darker shade, said colors being defined hereinafter in the detailed description. The new plant and flower is striking in that it combines certain characteristics of its parents, while being different from each, primarily in the form of its flower. The bloom brings to mind the variety Elegans, unpatented and its sport, C. M. Wilson, unpatented, but it is more spectacular than either in its large peony-like center and unusual depth.

The plant is of sturdy, bushy, compact, upright, medium growth and the blooming period is from middle to late season.

Asexual reproduction of this new variety has been by slipping and grafting in Oakland, California, and in the Santa Cruz Mountains, California, and has shown that it holds its characteristics through succeeding propagations.

The accompanying color drawing shows a typical specimen of the flower, bud and leaves of the new variety.

The following is a detailed description of this new variety, based upon observations made at Oakland, California, with color terminology in accordance with the Dictionary of Color by A. Mertz and M. P. Paul.

Breeding: Seedling.

*Seed parent.*—Seed picked from *Camellia japonica*, variety Princess Bachiocchi.

*Pollen parent.*—Presumed to be *Camellia japonica*, variety Kumasaka (because conditions were favorable and because of the remarkable and easily recognized affinity of the seedling for its parents, combining various characteristics of each).

Propagation: Holds its characteristics through succeeding propagations by slipping and grafting.

Bud: Close affinity to Kumasaka, but larger.

*Size.*—Large; about 1½" long from base of calyx and 2½"–3" circumference at tips of calyx.

*Form.*—Nearly round with pointed tip.

*Color.*—Rose, same as bloom, described below.

*Calyx.*—Generally eight sepals—imbricated—two inner longer (1½") than others—tinged rose, same as bloom—glabrous.

*Borne.*—Supernumerary—both on axils and terminals, in great numbers.

Bloom:

*Petalage.*—Semi-double to peony—Kumasaka. Outer guard petals flat, single row, usually 13—Princess Bachiocchi. Fairly regularly arranged, sometimes completely concealed by center petals, which are very irregular and convoluted with many petaloids mixed with stamens, both united with corolla. Lasts 2 to 4 days as cut; 5 to 7 days on plant; holds well as corsage.

*Color.*—Rose, Plate 1, section F, 5, with veining of petals slightly darker, about section J, 5 of Plate 1—close affinity to Kumasaka.

*Size.*—Large—4"–5½" in full bloom. Exceptionally deep—1½"–2½".

*Form.*—First opens sometimes with a rosebud center—affinity Kumasaka, then as a cup—Kumasaka, and retains it until nearly full bloom when guard petals—Princess Bachiocchi—usually visible, are flat and flower center assumes anemone or peony-like form.

*Petals.*—Medium thickness, soft. Guard petals heart shape with just a hint of indent at top. slight veining.

*Arrangement.*—Imbricated in guard—very irregular and convoluted in center. Numerous petaloids.

Fruit: A dehiscent, caps—glabrous.

Genital organs:

*Stamens, anthers.*—Medium size; many.

*Color.*—Yellow, Plate 9, section L, 6, called "golden glow."

*Pollen.*—Yellow, sometimes golden.

*Arrangement.*—Interspersed with petals and numerous petaloids, almost hidden.

*Stamens, filaments.*—Short to medium length. Color—straw-yellow, Plate 9, section E, 1, lighter at base when combined with petaloids.

Form of plant and growth: Close affinity to Princess Bachiocchi (seed parent) and Kumasaka (assumed to be pollen parent). Upright as with Kumasaka but broader, sturdier; heavily branched—bushy and compact as with Princess Bachiocchi.

Foliage:

*Size.*—Large, 4"–5½" long, 2½" wide—affinity to Princess Bachiocchi.

*Quantity.*—Abundant.

*Color.*—Close affinity to Princess Bachiocchi (dark green on top, Plate 24, section L, 6, lighter on back, Plate 22, section L, 2).

*Shape.*—Affinity to Princess Bachiocchi (oval) with ½" apices. Medium serration—from Kumasaka.

*Texture.*—Affinity to Princess Bachiocchi (heavy).

*Ribs and veins.*—Moderately prominent on both sides.

I claim:

A new and distinct variety of Camellia plant substantially as illustrated and described, characterized by its flower of medium to large diameter but of exceptional depth, by its rose colored semi-double to anemone-peony form of flower, with center petals heavily convoluted with stamens and numerous petalloids intermixed and peony-like center of unusual depth, the outer guard petals usually being flat, in a single row, lightly veined and in slightly darker hue than the center part of the flower, and by its setting of many flower buds, said buds being exceptionally large size, approximating one and one-half inches in length from base of calyx and two and one-half to three inches in circumference at tip of calyx.

No references cited.